US011174857B1

(12) United States Patent
Kowalski et al.

(10) Patent No.: US 11,174,857 B1
(45) Date of Patent: Nov. 16, 2021

(54) DIGITAL PRESSURE SWITCH SYSTEMS AND METHODS

(71) Applicant: GENERAL AIR PRODUCTS, INC., Exton, PA (US)

(72) Inventors: Trent J. Kowalski, Reading, PA (US); Ron E. McClellan, Oxford, PA (US); Richard A. West, Montgomery, TX (US)

(73) Assignee: GENERAL AIR PRODUCTS, INC., Exton, PA (US)

(*) Notice: Subject to any disclaimer, the term of this patent is extended or adjusted under 35 U.S.C. 154(b) by 0 days.

(21) Appl. No.: 17/104,594

(22) Filed: Nov. 25, 2020

(51) Int. Cl.
*F04B 49/06* (2006.01)
*F04B 49/02* (2006.01)
(Continued)

(52) U.S. Cl.
CPC ....... *F04B 49/065* (2013.01); *A61M 5/16854* (2013.01); *A62C 37/04* (2013.01); *F04B 49/022* (2013.01); *F04B 49/03* (2013.01); *F04B 49/06* (2013.01); *F04B 49/08* (2013.01); *A61M 2205/18* (2013.01); *A61M 2205/50* (2013.01); *A61M 2205/581* (2013.01); *A62C 37/50* (2013.01); *F04B 51/00* (2013.01);
(Continued)

(58) Field of Classification Search
CPC .......... A61M 5/16854; A61M 2205/18; A61M 2205/50; A61M 2205/581; A62C 37/50; A62C 37/04; F04B 49/06; F04B 49/065; F04B 2203/0201; F04B 2205/01; F04B 2205/03; F04B 2205/05; F04B 49/022; F04B 49/08; F04B 51/00; F04B 49/03; F04C 2270/80; F04C 28/28; F04D 15/00; F04D 15/0088
See application file for complete search history.

(56) References Cited

U.S. PATENT DOCUMENTS 4,336,001 A * 6/1982 Andrew ................ F04B 49/065
417/282
4,611,290 A * 9/1986 Henningsen ....... G05D 16/2066
169/13
(Continued)

FOREIGN PATENT DOCUMENTS

WO 2015134914 A1 9/2015

OTHER PUBLICATIONS

"Control Relays and Timers", vol. 7—Logic Control, Operator Interface and Connectivity Solutions, Feb. 2014, 208 pages.
(Continued)

*Primary Examiner* — Peter J Bertheaud
(74) *Attorney, Agent, or Firm* — Buchanan, Ingersoll & Rooney PC

(57) ABSTRACT

A digital pressure switch is configured to be connected to a fluid pump. The digital pressure switch includes a pressure sensor configured to measure pressure inside a closed system, one or more relays configured to be connected to the fluid pump for activation and deactivation of the fluid pump, an amperage sensor configured to measure an amperage draw of an electric motor of the fluid pump, and a controller configured to process data from the pressure sensor and/or data from the amperage sensor and to activate or deactivate the motor of the fluid pump based on the data from the pressure sensor and/or the data from the amperage sensor, using the relays.

23 Claims, 15 Drawing Sheets

(51) Int. Cl.
    *F04B 49/03*     (2006.01)
    *F04B 49/08*     (2006.01)
    *F04C 28/28*     (2006.01)
    *A62C 37/36*     (2006.01)
    *A61M 5/168*     (2006.01)
    *A62C 37/50*     (2006.01)
    *F04D 15/00*     (2006.01)
    *F04B 51/00*     (2006.01)

(52) U.S. Cl.
    CPC ... *F04B 2203/0201* (2013.01); *F04B 2205/01* (2013.01); *F04B 2205/03* (2013.01); *F04B 2205/05* (2013.01); *F04C 28/28* (2013.01); *F04C 2270/80* (2013.01); *F04D 15/00* (2013.01); *F04D 15/0088* (2013.01)

(56) References Cited

U.S. PATENT DOCUMENTS

| | | | |
|---|---|---|---|
| 5,221,189 A * | 6/1993 | Henningsen | F04B 49/022 |
| | | | 417/12 |
| 5,950,150 A * | 9/1999 | Lloyd | A62C 37/50 |
| | | | 340/506 |
| 6,315,523 B1 * | 11/2001 | Mills | F04B 47/02 |
| | | | 307/150 |
| 9,453,505 B2 * | 9/2016 | Stephens | F04B 49/065 |
| 10,030,647 B2 * | 7/2018 | Ortiz | F04D 13/0686 |
| 10,240,593 B2 | 3/2019 | Stephens | |

OTHER PUBLICATIONS

"Digital Air Maintenance Device (AMD) GEN-3 with Leak Detection", C-AIRE Compressors, S281R-LD1-115PD, 2 pages, Sep. 2019.

"GPRS Miniature Wireless Pressure Sensor, PT701 Wireless Pressure Transducer", Atech Sensor, 4 pages, 2019.

"Retrofit Air Compressors With Full Automation", Compressor Controller, 5 pages, 2019.

\* cited by examiner

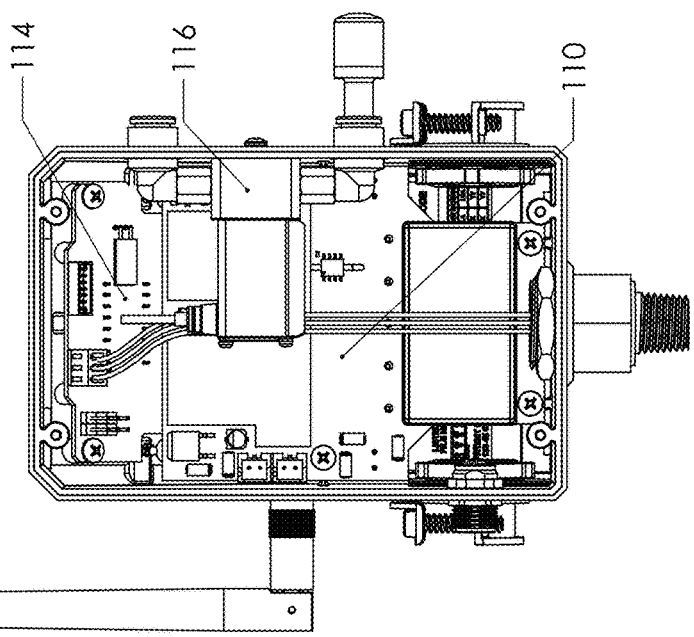
FIG. 3G
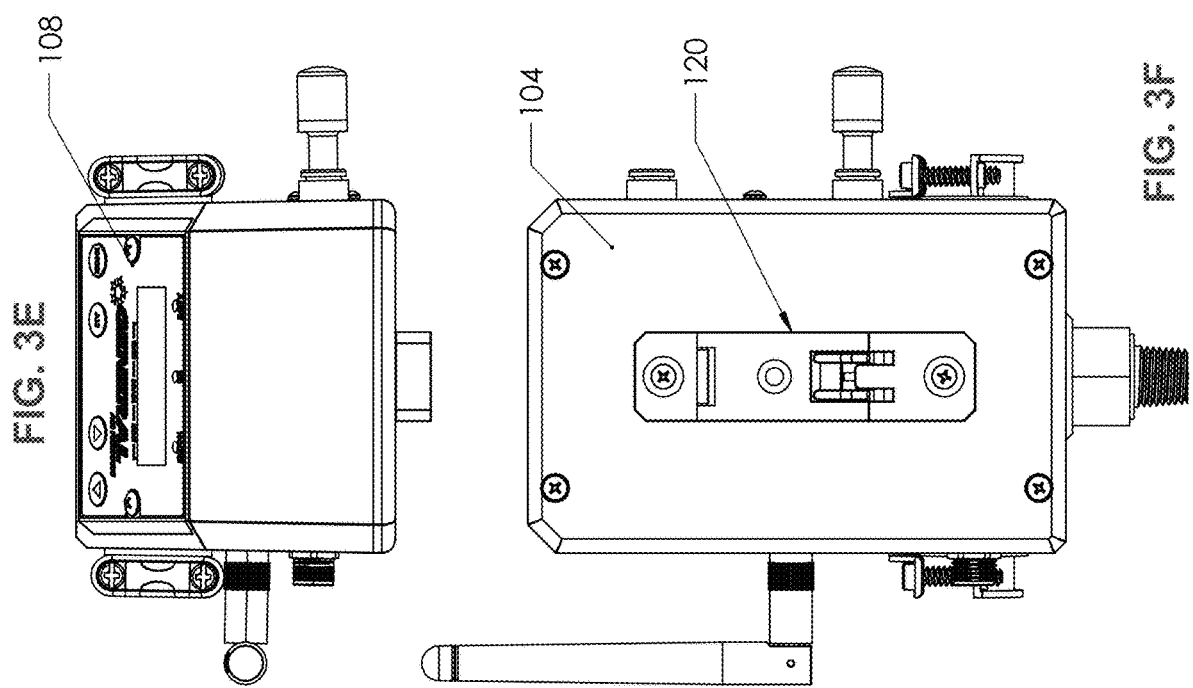
FIG. 3E
FIG. 3F

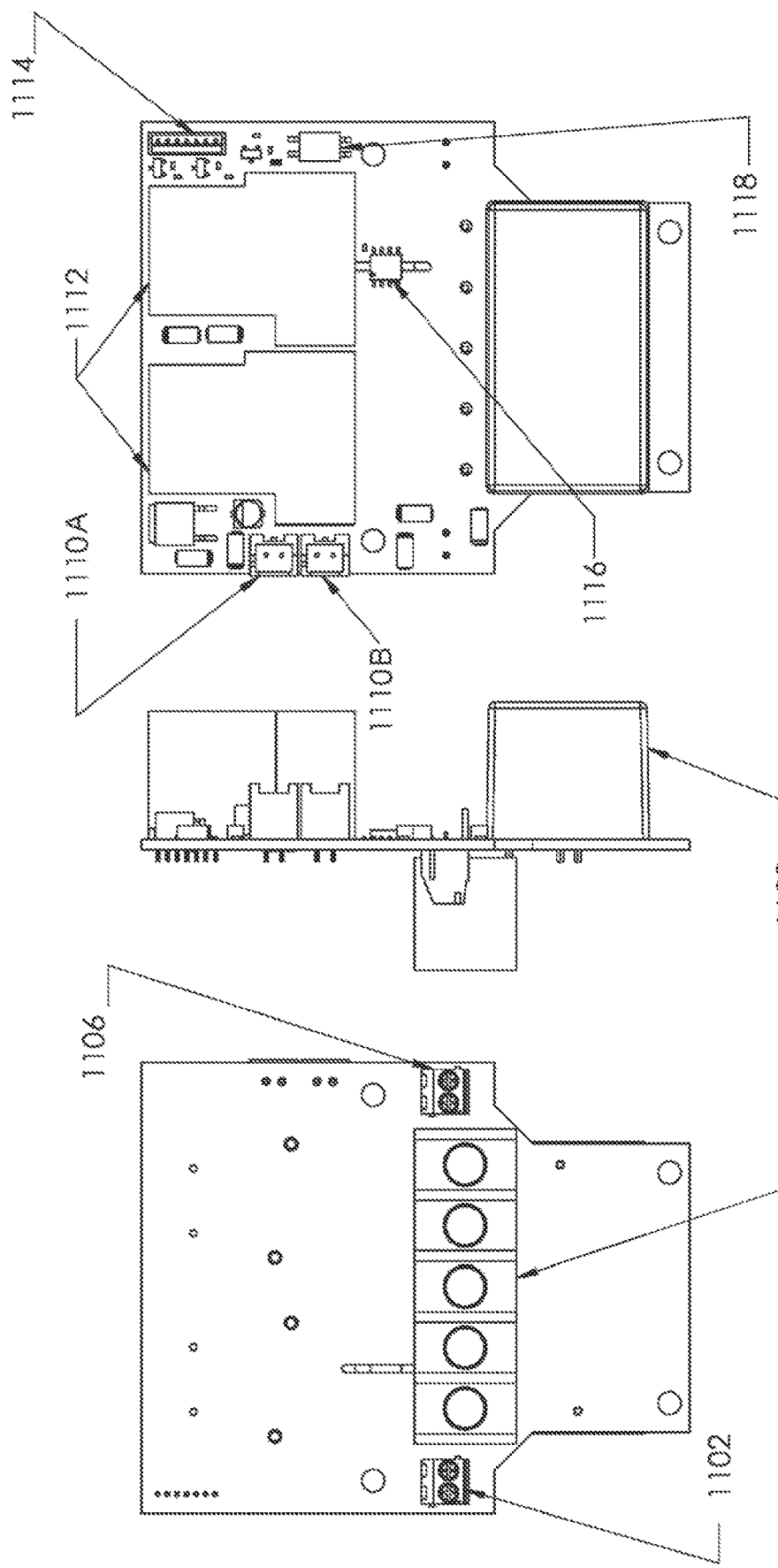

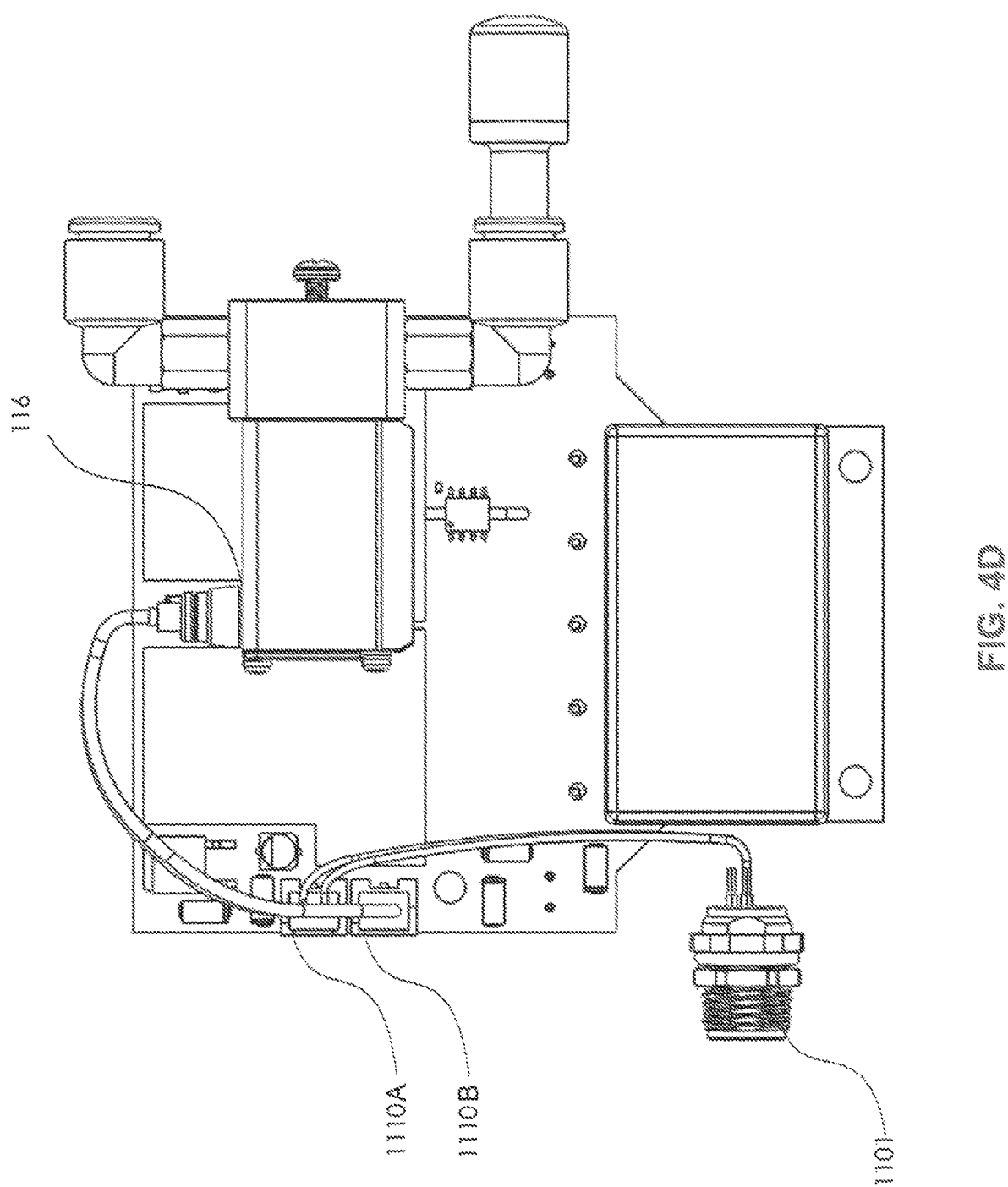

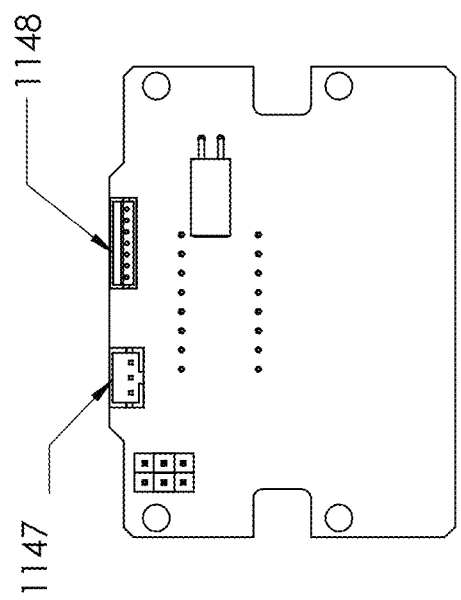
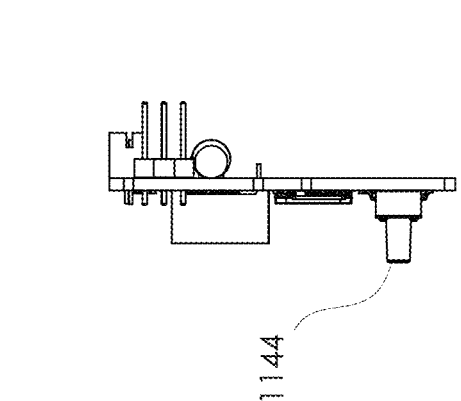
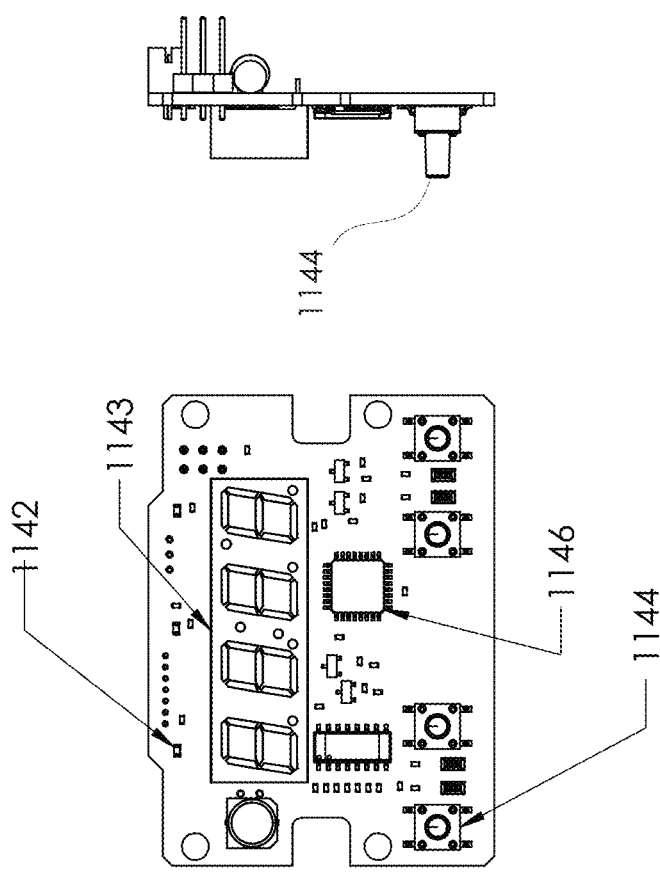
FIG. 5C
FIG. 5B
FIG. 5A

| | INITIAL MEASUREMENT 8/1/2019 | LAST MEASUREMENT 8/28/2019 | AVERAGE | % DIFFERENCE FROM INITIAL | % DIFFERENCE FROM AVERAGE |
|---|---|---|---|---|---|
| LEAK RATE | 1.4 PSI/HR | 1.8 PSI/HR | | | |
| CYCLE RATE | 5 CYCLES/WEEK | 6 CYCLES/WEEK | | | |
| POWER? | OK | OK | | | |
| BATTERY LEVEL | 99% | 99% | | | |
| ON PRESSURE | 27.6 | 28.2 PSI | | | |
| OFF PRESSURE | 38.5 | 39 PSI | | | |
| PUMP UP TIME | 14min 30sec | 14min 48sec | | | |
| VALVE TRIP TIME (if loss of power) | 3hrs. 45min. | 3hrs. 25min. | | | |

DIGITAL PRESSURE SWITCH SYSTEMS AND METHODS

TECHNICAL FIELD

The present disclosure relates to a digital pressure switch, and a method of using the same.

BACKGROUND INFORMATION

Conventional dry pipe and pre-action fire sprinkler systems rely on a pressure sensing switching device as its primary source of operation. In most cases, this switching device is mechanical: a spring and diaphragm which opens and closes mechanically based off of the measured pressure. This type of switch is commonly referred to as a pressure switch.

Conventional mechanical pressure switches rely on spring tension and as a result can suffer from any of the following: a limited range of adjustability, a drift in pressure ON/OFF settings due to changes in ambient air temperature, adjustments to the pressure ON/OFF settings which expose technicians to high voltage, and calibration of the pressure setting which typically relies on an analog pressure gauge (and thus may lack precision).

Moreover, measuring the amperage draw of an electric motor may subject a technician to high voltage.

Fluid pumps can also "short cycle," whereby the fluid pump turns ON and OFF very frequently due to rapid changes in downstream pressure. Mechanical pressure switches have no way of detecting this rapid cycling.

Dry pipe sprinkler and pre-action systems can also suffer from an increasing leak rate through the life of the piping system. Because of this, air compressors run for longer periods of time and more frequently to keep up with the increasing leakage; this can lead to premature failure of the air compressor.

Power outages are another problem in dry pipe and pre-action systems. In case of a power outage, compressed air cannot be delivered to the system.

Per National Fire Protection Association requirements, dry pipe and pre-action systems require a 0-40 PSI pump up time in no more than 30 minutes. Over time, compressor flow rates slowly deteriorate from normal wear, which may result in the overall fill time to take more than 30 minutes. Troubleshooting a leaky dry pipe system or a possible bad compressor can take a great deal of time and be very expensive.

SUMMARY

A digital pressure switch is configured to be connected to a fluid pump. The digital pressure switch includes a pressure sensor configured to measure pressure inside a closed system, one or more relays configured to be connected to the fluid pump for activation and deactivation of the fluid pump, an amperage sensor configured to measure an amperage draw of an electric motor of the fluid pump, and a controller configured to process data from the pressure sensor and/or data from the amperage sensor and to activate or deactivate the motor of the fluid pump based on the data from the pressure sensor and/or the data from the amperage sensor, using the relay(s).

A method of monitoring a closed system uses a digital pressure switch configured to be connected to a fluid pump. The digital pressure switch includes a pressure sensor configured to measure pressure inside the closed system, one or more relays configured to be connected to the fluid pump for activation and deactivation of the fluid pump, an amperage sensor configured to measure an amperage draw of an electric motor of the fluid pump, a communication module configured to communicate measurement data to an external server, and a controller configured to process data from the pressure sensor and/or data from the amperage sensor and to activate or deactivate the motor of the fluid pump based on the data from the pressure sensor and/or the data from the amperage sensor, using one or more relays. The method includes acquiring pressure data from the pressure sensor, the pressure data being representative of pressure inside the closed system.

BRIEF DESCRIPTION OF THE DRAWINGS

Other features and advantages disclosed herein will become more apparent from the following detailed description of illustrative embodiments when read in conjunction with the attached drawings.

FIG. 3E is a schematic representation of a top view of an illustrative digital pressure switch.

FIG. 3F is a schematic representation of a rear view of an illustrative digital pressure switch with optional DIN rail adapter.

FIG. 3G is a schematic representation of a rear view of an illustrative digital pressure switch, with the rear cover and the DIN rail adapter hidden.

FIG. 4A is a schematic representation of a front view of an illustrative power supply and relay PCB.

FIG. 4B is a schematic representation of a side view of an illustrative power supply and relay PCB.

FIG. 4C is a schematic representation of a rear view of an illustrative power supply and relay PCB.

FIGS. 4D-F are schematic representations of alternative illustrative power supply and relay PCB configurations.

FIG. 5A is a schematic representation of a front view of an illustrative LED control PCB.

FIG. 5B is a schematic representation of a side view of an illustrative LED control PCB.

FIG. 5C is a schematic representation of a rear view of an illustrative LED control PCB.

FIG. 6 shows an illustrative customer report.

DETAILED DESCRIPTION

Figure 1A:
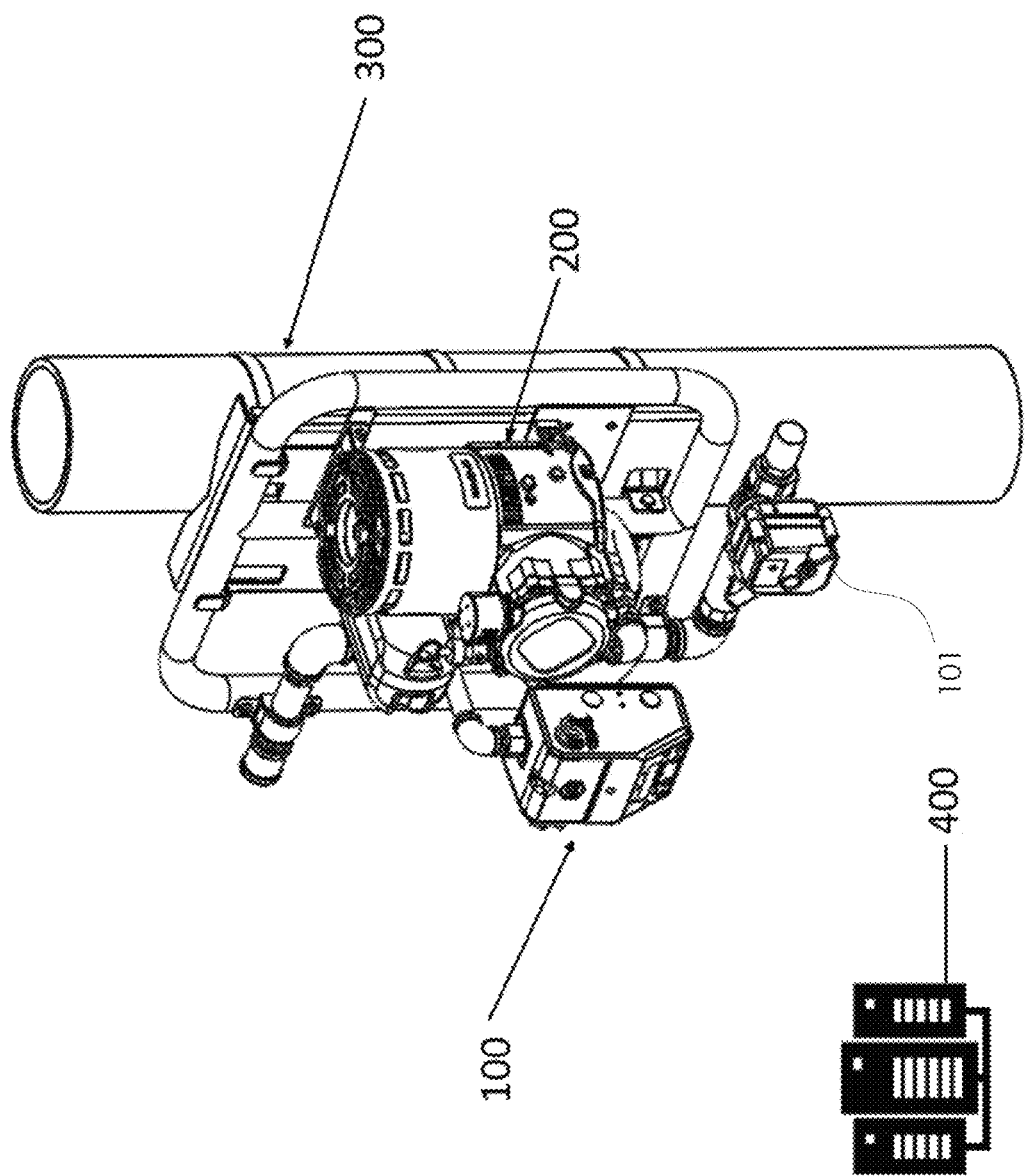
FIG. 1A is a schematic representation of an illustrative system including a digital pressure switch and fluid pump mounted on piping.

FIG. 1A shows an illustrative embodiment of a system including a digital pressure switch 100 and fluid pump 200 mounted on piping 300 (or any other closed system, such as, but not limited to, a tank or tubing). In this example, the digital pressure switch 100 is mounted to the piping 300 downstream from the fluid pump 200, and is configured to communicate with a data server 400.

Figure 1B:
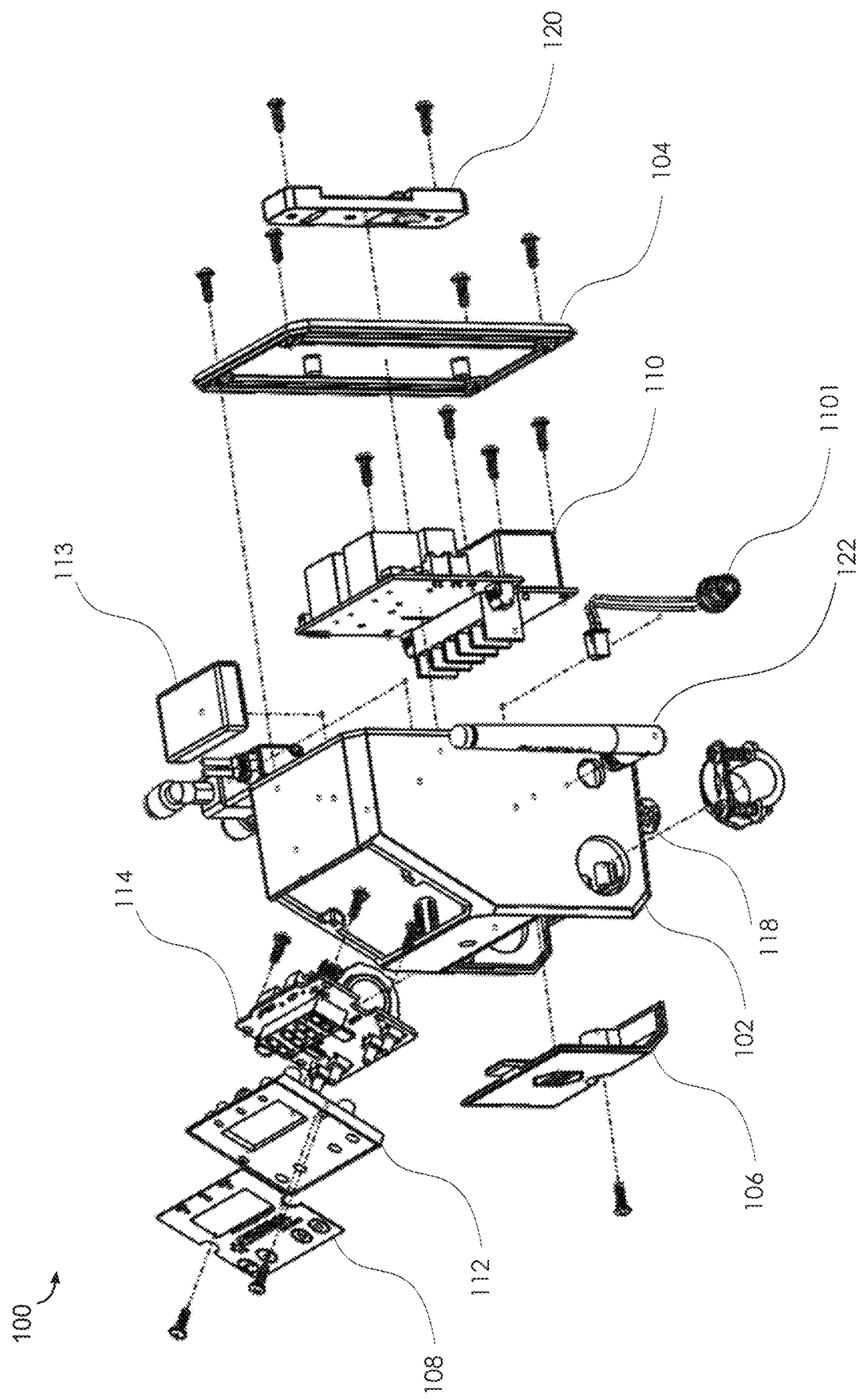
FIGS. 1B-1C are schematic exploded views of an illustrative digital pressure switch.
Figure 1C:
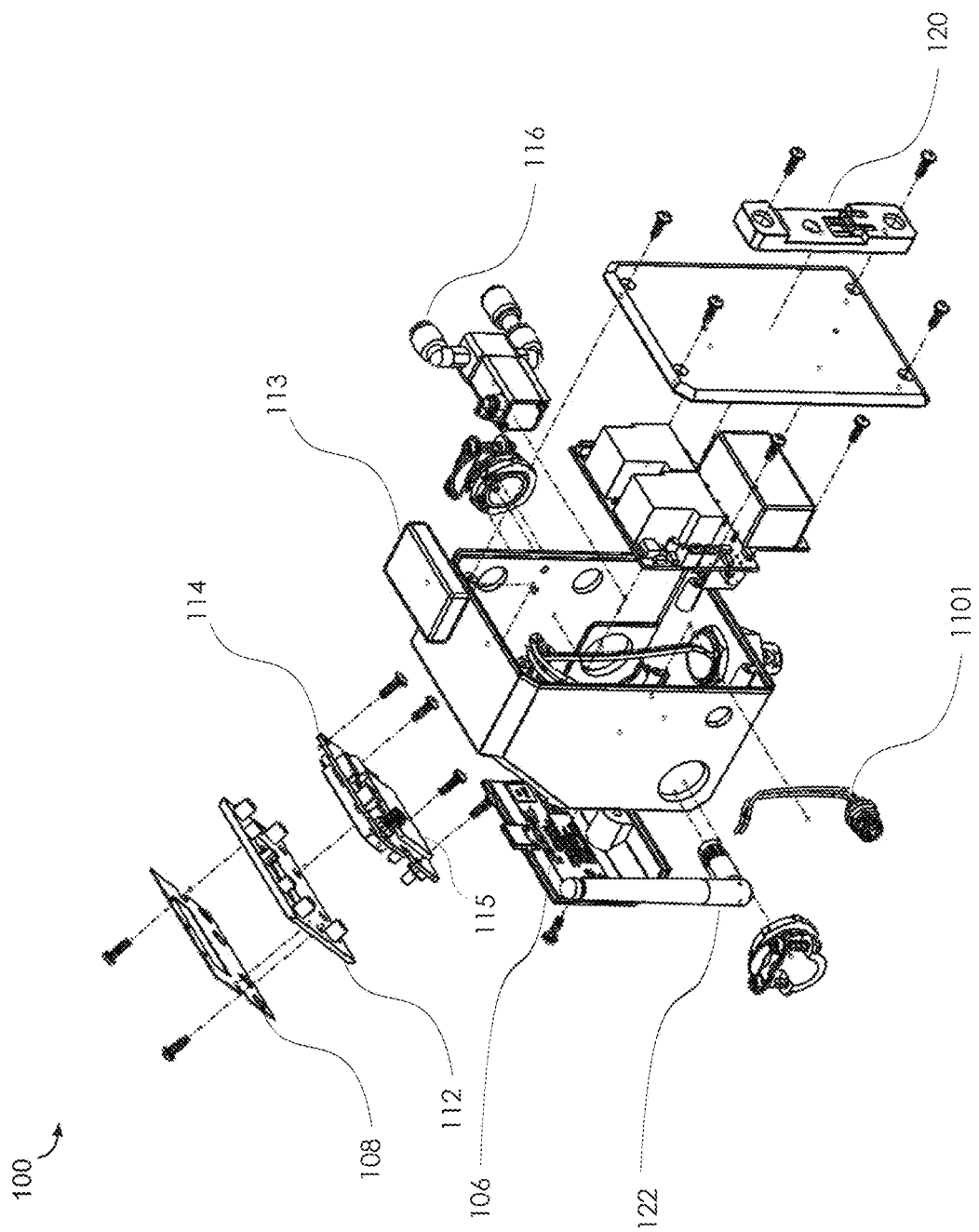

FIGS. 1B-1C show an exploded view of an illustrative digital pressure switch 100, which includes a housing. In FIGS. 1B-1C, the housing includes a front housing 102, a rear cover 104, a terminal access cover 106 and a display cover (e.g., with overlay 108) 112. The front housing 102 houses a power supply and relay printed circuit board (PCB) 110, a lithium ion battery 113, and a light-emitting diode (LED) control PCB 114 positioned behind the display cover 112. The power supply and relay PCB 110 can use the microprocessor of the LED control PCB 114. The housing is also equipped with an unloading valve with fittings 116, a pressure sensor fitting 118, and a DIN rail adapter 120. In illustrative embodiments, the digital pressure switch 100 measures pressure through the pressure sensor fitting 118 to determine if a fluid pump should be ON or OFF. In illustrative embodiments, the digital pressure switch 100 can also include a communication module 115 (e.g., wired or wireless, such as Wi-Fi or cellular), for example on or connected to the LED control PCB 114 or to the power supply and relay PCB 110, and configured to communicate measurement data to an external server 400. An antenna 122 is also provided to amplify wireless signals. A panel mount connector 1101 can be provided for direct connection to the power supply and relay PCB 110.

In illustrative embodiments, a digital pressure switch 100 is configured to measure pressure, e.g., by means of a controller and a pressure sensor coupled to the pressure sensor fitting 118. For example, the switching device in a dry pipe or pre-action fire sprinkler system can control the electrical power to a motor, which drives a fluid pump, such as, but not limited to an air compressor, a water pump, or a vacuum pump. The electrical power to a motor is switched ON and OFF based on a user configurable setting (e.g., turned ON at 10 psig and turned OFF at 20 psig). Dry pipe and pre-action fire sprinkler systems are the primary applications for the digital pressure switch disclosed herein, though any closed system, including any pressurized fluid system (e.g., between 0 and 150 psig) which relies on a motor with an electrical load can benefit from embodiments of the digital pressure switch described herein.

Figure 2A:
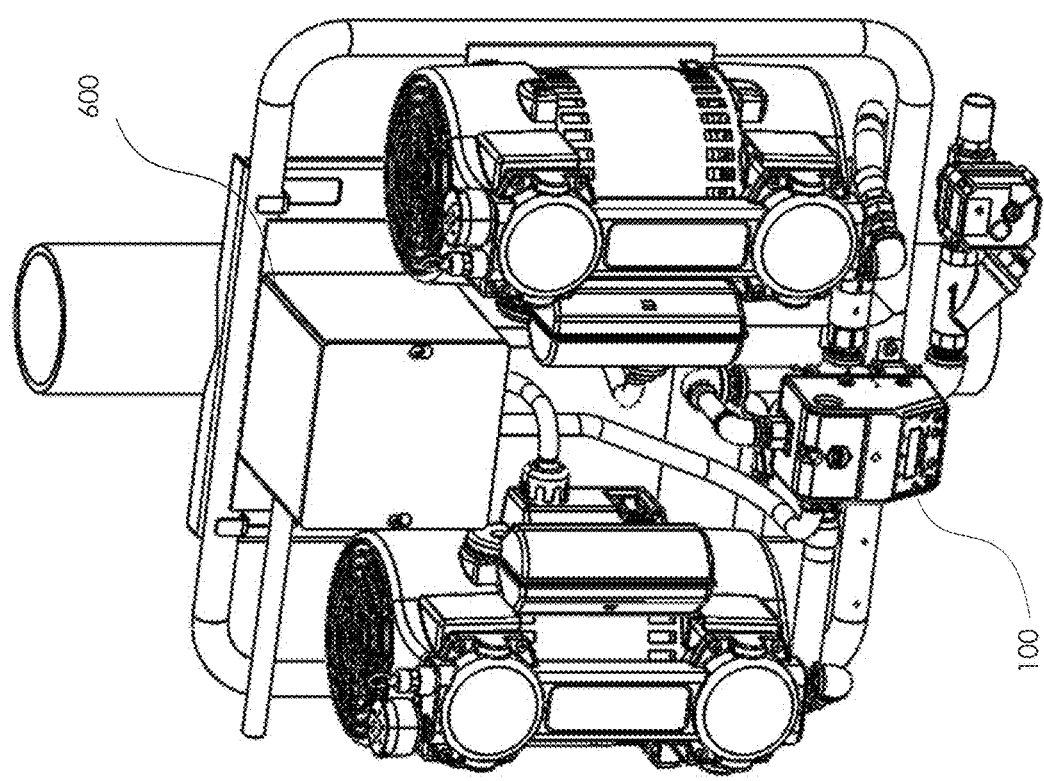
FIG. 2A is a schematic representation of an illustrative digital pressure switch used as a pilot operating device to control a higher power contactor or motor starter.

FIG. 2A shows an illustrative digital pressure switch 100 used as a pilot device, wherein the digital pressure switch can electrically actuate a higher power motor contactor or motor starter. In FIG. 2A, the enclosure 600 includes a higher power motor contactor or motor starter (not shown). When used as a pilot device, a digital pressure switch may control the electrical power to 3-phase motors or 1-phase higher horsepower motors.

In illustrative embodiments, a connected remote monitoring digital pressure switch is used to measure various parameters of a fluid pump and a dry pipe or pre-action fire sprinkler system. One function of such a digital pressure switch is to switch the electrical load to the motor ON and OFF based on user configurable pressure settings.

In illustrative embodiments, the digital pressure switch is configured to measure fluid pressure and is configured to scale the signal to be viewed on a digital LED display.

In illustrative embodiments, ON and OFF fluid pump settings can be configured to a desired range or value.

In illustrative embodiments, the digital pressure switch is configured to switch an electrical signal of desired characteristics to an electric motor using one or more relays, preferably two.

In illustrative embodiments, the digital pressure switch is configured to determine and record fluid pump run hours.

In illustrative embodiments, the digital pressure switch is configured to determine and record the number of cycles of a fluid pump.

In illustrative embodiments, the digital pressure switch is configured to determine and record a fluid pump cycle rate. If cycles occur too frequently (e.g., compared to a predetermined frequency), the digital pressure switch can trigger an alarm signal (e.g., auditory, visual, or other).

In illustrative embodiments, the digital pressure switch is configured to actuate an electric valve for unloading fluid from the fluid pump head after turning OFF. In illustrative embodiment, as shown for example in FIG. 1A, this same electrical signal can be used to actuate a valve 101 installed outside of the digital pressure switch enclosure. In this case, this external valve 101, connected using a panel mount connector 1101, can act simultaneously as a drain and an unloader for the fluid pump piping upstream from a pressurized vessel.

Figure 2B:
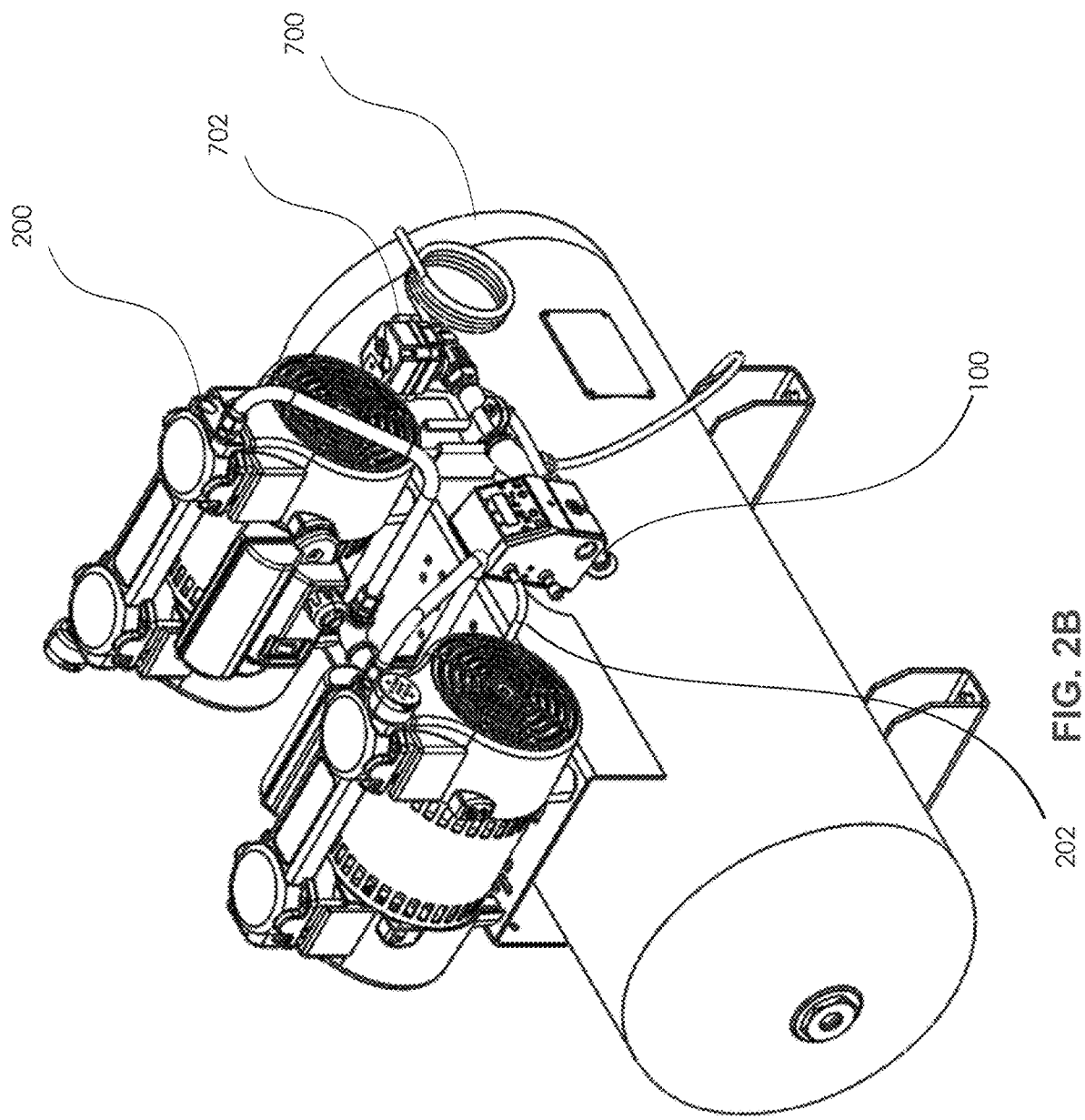
FIG. 2B is a schematic representation of an illustrative digital pressure switch operating an internal unloading electric valve and an external drain valve simultaneously.

In an illustrative embodiment, the panel mount connector 1101 is connected to an alternate electrical circuit; in which case the alternate electrical circuit will operate on a user configurable ON and OFF timer. The alternate user configurable timed electrical circuit is configured to act as a drain for excess fluid in a pressurized vessel downstream from a fluid pump. In an illustrative embodiment, the panel mount connector 1101 is connected to the alternate user configurable timed electrical circuit and simultaneously an electric valve is connected to the unloading valve electrical circuit which is configured to unload fluid from a fluid pump head. An example of this configuration is shown in FIG. 2B, which illustrates an embodiment in which an unloading line 202 of a fluid pump 200 is connected to an internal unloading electric valve 116 of the digital pressure switch 100, and the drain valve 702 of a tank vessel 700 is connected to the panel mount connector 1101 of the digital pressure switch 100.

In illustrative embodiments, the digital pressure switch is configured to measure the amperage draw of an electric motor, compare this value to a predetermined limit value and trigger a remote alarm signal. This can provide a mechanism for predictive failure detection. In illustrative embodiments, examples of remote alarm signals can indicate any or any combination of the following: fluid pump short cycling, high amperage, fluid pump exceeding a predetermined runtime (e.g., 30 minutes), and fluid pump failure to start.

In an alternative illustrative embodiment, the digital pressure switch may be configured to record the peak motor amperage on fluid pump startup.

In illustrative embodiments, the digital pressure switch can be mounted on a DIN rail (e.g., a 35 mm DIN rail).

In illustrative embodiments, the following can be provided from measurements obtained by the digital pressure switch, either locally or by an external device (e.g., a server, local or cloud), optionally in communication with the digital pressure switch: fluid pump runtime monitoring, fluid pump ON and OFF pressure set-points, fluid pump cycling rate, dry pipe or pre-action sprinkler system leak rate (e.g., in PSI/HR or SCFM/HR), power loss monitoring, monitoring of time until sprinkler system valve trips in case of power loss, estimation of predictable fluid pump maintenance based off of fluid pump model and measured runtime (e.g., using a vibration sensor, as vibrations increase over time and use of the device).

Figure 3B:
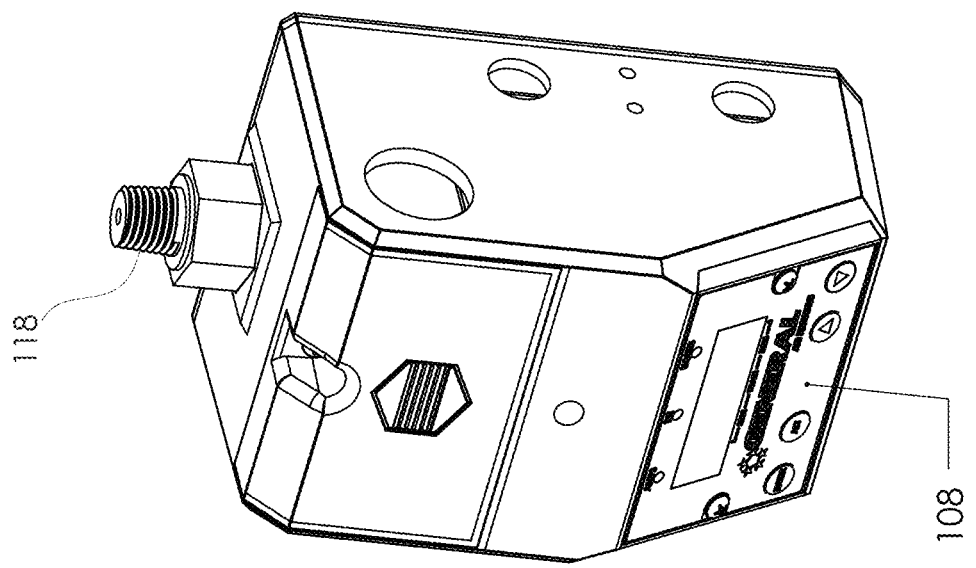
FIG. 3B is a schematic representation of a perspective view of an illustrative digital pressure switch in a second configuration with the pressure sensor fitting at the top.
Figure 3A:
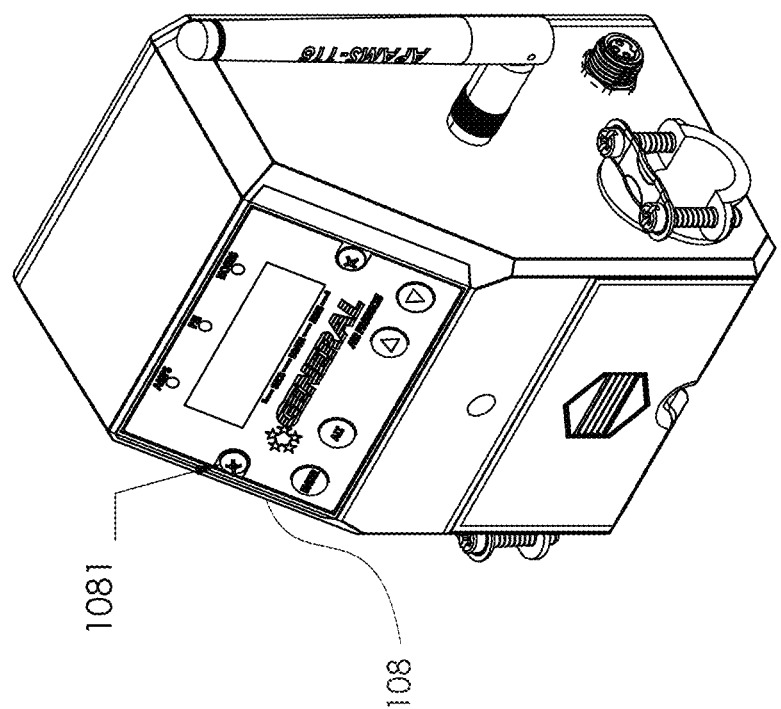
FIG. 3A is a schematic representation of a perspective view of an illustrative digital pressure switch in a first configuration with the pressure sensor fitting at the bottom.
Figure 3D:
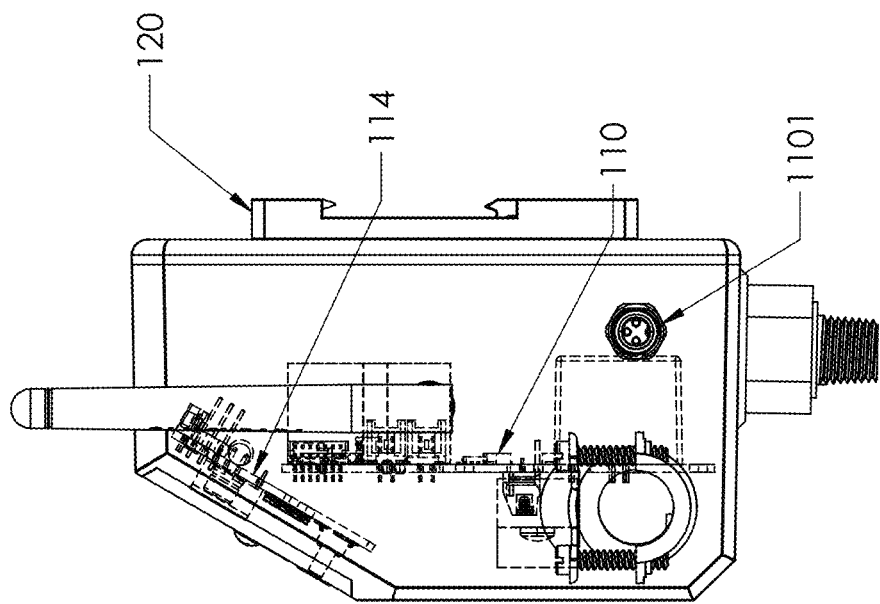
FIG. 3D is a schematic representation of a side view of an illustrative digital pressure switch with a portion of the housing hidden to show the internal power supply and relay PCB.

FIGS. 3A-3G show various views of an illustrative embodiment of a digital pressure switch 100. FIG. 3A shows a configuration in which the digital pressure switch 100 is oriented such that the pressure sensor fitting 118 (not visible) is at the bottom. By removing and rotating the display cover 112 and LED control PCB 114 by 180 degrees (e.g., using mounting screws 1081 and corresponding holes, e.g., in the housing), the digital pressure switch 100 can be positioned in an inverted orientation, with the pressure sensor fitting 118 at the top, as shown in FIG. 3B. One of these two configurations may be preferable depending on the setting. This functionality, in illustrative embodiments, can be enabled by virtue of the LED control PCB 114 and the power supply and relay PCB 110 being separate boards, thus allowing the LED control PCB 114 to be rotated relative to the power supply and relay PCB 110.

Figure 3C:
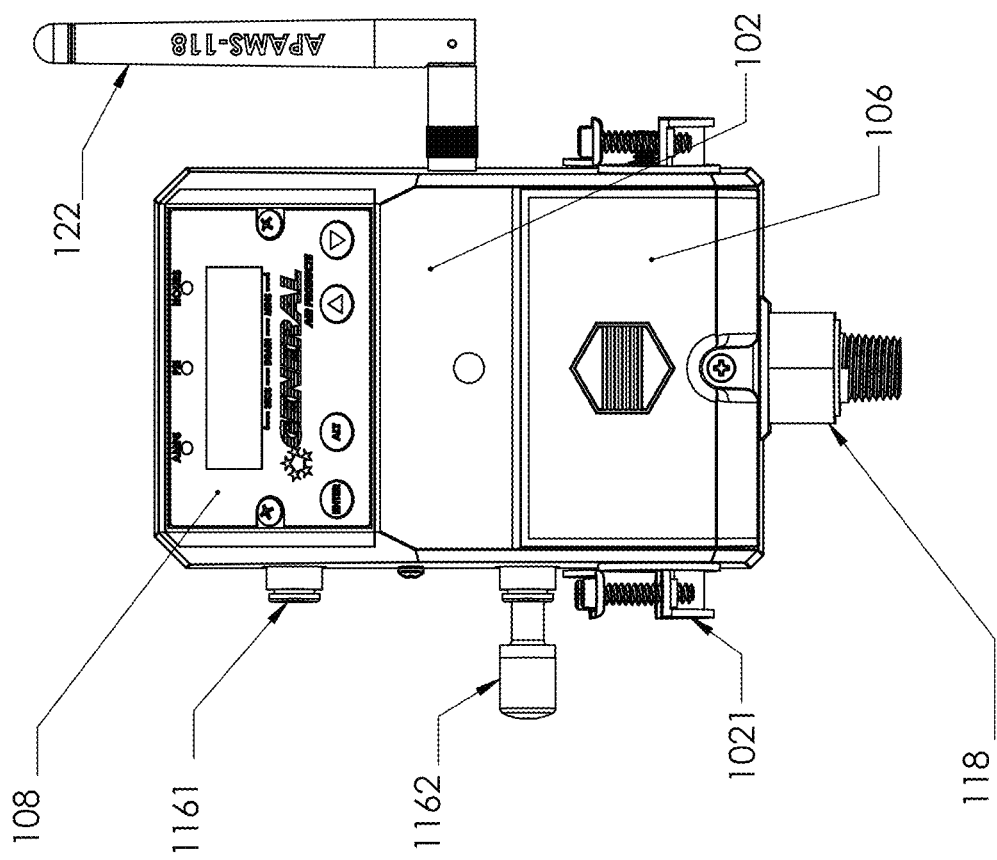
FIG. 3C is a schematic representation of a front view of an illustrative digital pressure switch.

As shown for example in FIG. 3C, an illustrative digital pressure switch 100 includes an unloading valve inlet port 1161 and an unloading valve muffler 1162. A cord grip 1021 can be used for cord management. A panel mount connector 1101 can be provided for direct connection to the PCB 110. The antenna 122 is also provided to amplify wireless signals.

Figure 4F:
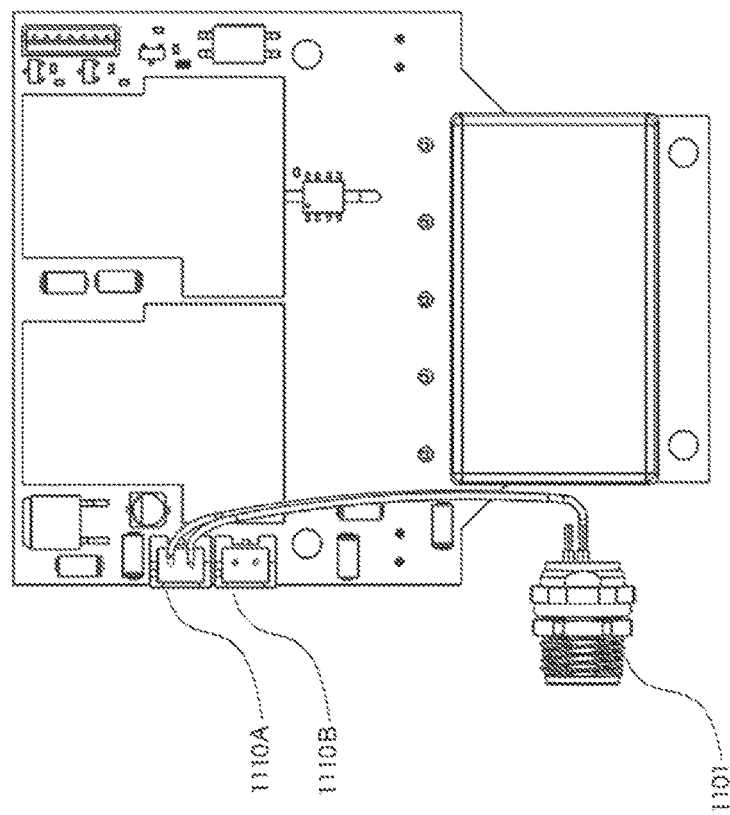

FIGS. 4A-4C show various views of an illustrative embodiment of a power supply and relay PCB 110, which includes alarm terminals 1102, a barrier terminal block 1104, input terminals 1106 (e.g., +24 vdc), a power supply 1108, valve connectors 1110A and 1110B, relays 1112, an I/O connector 1114 (e.g., a 7-pin connector), an amperage sensor 1116, and an alarm relay 1118.

In illustrative embodiments, the alarm terminals 1102 provide a point of wire termination for the alarm relay 1118.

In illustrative embodiments, the barrier terminal block 1104 provide a point of wire termination for supplying power to the digital pressure switch and to an electric motor of a fluid pump.

In illustrative embodiments, the input terminals 1106 provide a point of wire termination for an external power supply (e.g., a 24 VDC power supply.

In illustrative embodiments, the power supply 1108 is an internal power supply (e.g., 24 VDC). Alternatively, the power supply 1108 can be replaced by input terminals 1106 connectable to an external source of power (e.g., 24 VDC).

Figure 4E:
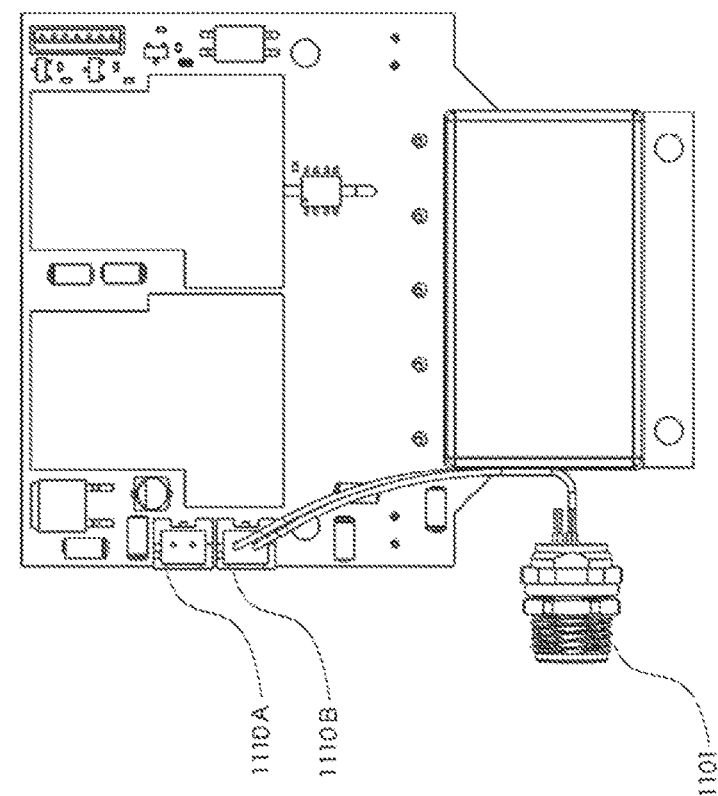

In illustrative embodiments, the valve connectors 1110A and 1110B provide a point of wire termination for valves, such as a drain valve or an unloading valve. For example, in FIG. 4D, which provides an example of connectivity for the illustrative embodiment shown in FIG. 2B, the upper valve connector 1110A is a connector of a configurable timed drain valve electrical circuit, and is connected to the panel mount connector 1101, while the lower valve connector 1110B is a connector of an unloading valve electrical circuit and is connected to an internal electric valve 116. Alternatively, as shown for example in FIG. 4E, the panel mount connector 1101 can be connected to an unloading valve electrical circuit at the lower valve connector 1110B. In this instance, a larger external valve may be used to remove fluid and particulates from a fluid pump head. Alternatively, as shown for example in FIG. 4F, the panel mount connector 1101 can be connected to a configurable timed drain valve electrical circuit at the upper valve connector 1110A, and the unloading valve electrical circuit at the lower valve connector 1110B may not be connected. The position of the valve connectors 1110A and 1110B in the figures is illustrative only—the connectors can be interchanged or relocated elsewhere on the PCB.

In illustrative embodiments, the relays 1112 are configured to control power to a fluid pump, in order to activate and deactivate the pump.

In illustrative embodiments, the amperage sensor 1116 is configured to measure amperage draw of an electric motor of a fluid pump.

In illustrative embodiments, the alarm relay 1118 is configured to connect to and actuate an alarm (e.g., visual, auditory or other).

FIGS. 5A-C show various views of an illustrative embodiment of an LED control PCB 114, which includes discreet LED indicators 1142, an LED display 1143, push buttons 1144, a controller (e.g., a microprocessor) 1146, a pressure sensor connector 1147, and an I/O connector 1148 (e.g., a 7-pin connector).

In illustrative embodiments, the LED indicators 1142 can provide a visual indication of the value being displayed on the LED display 1143. For example, three LED indicators 1142 might be labeled "AMPS", "PSI/BAR" and "HOURS" on the display overlay 108, indicating display of the amperage draw from the fluid pump motor, the pressure inside the closed system, or the fluid pump runtime.

In illustrative embodiments, the push buttons 1144 can be configured, for example, to toggle between values displayed on the LED display 1143, and/or to set various threshold settings associated with monitoring by the digital pressure switch. For example, four push buttons 1144 may be labeled "ENTER," "ALT," "UP" and "DOWN" to enable the above-noted functions. In alternative embodiments, instead of push buttons 1144, any suitable input device can be used, such as, but not limited to, other mechanical switching devices, or touch sensors.

In illustrative embodiments, the pressure sensor connector 1147 can be connected to a pressure sensor for pressure monitoring, via the pressure fitting 118. Values received through the pressure sensor connector 1147 can be interpreted by the controller 1146 and displayed on the LED display 1143.

In illustrative embodiments, the I/O connector 1148, which can be connected to the I/O connector 1114 of the power supply and relay PCB 110.

In illustrative embodiments, the digital pressure switch 100 is configured to activate or deactivate the motor of the fluid pump using the relays 1112, based on pressure data from a pressure sensor connected to the pressure sensor connector 1147, by comparing a measured pressure value to a predetermined threshold value.

In illustrative embodiments, the digital pressure switch 100 is configured to trigger an alarm (e.g., remote through a remotely generated user interface, or connected to the alarm relay 1118) based on pressure data from the pressure sensor connected to the pressure sensor connector 1147.

In an alternative illustrative embodiment, the digital pressure switch 100 may be configured to activate or deactivate the motor of the fluid pump based on amperage data from the amperage sensor 1116.

In illustrative embodiments, the digital pressure switch 100 is configured to trigger an alarm (e.g., remote through a remotely generated user interface, or connected to the alarm relay 1118) based on amperage data from the amperage sensor 1116.

In illustrative embodiments, during operation, when the fluid pump is ON, pressure is measured at a predetermined rate (e.g., 2 Hz) and is reported back to a data server. When the fluid pump is OFF, the data collection rate for pressure can be smaller (e.g., once every 15 minutes). An overall change in system pressure over time is used to calculate the system leak rate (e.g., in PSI/HR). Additionally, fluid pump life cycles, fluid pump cycling frequency, fluid pump runtime, amperage, alarm signals, overall life runtime, fluid pump ON and OFF setpoint pressures, battery level, sprinkler pipe valve trip time, and/or fluid pump maintenance can all be measured/calculated and reported to the data server. The data can be used to create a user interface and develop a customer report (e.g., a monthly report). An example of a report 450 is shown in FIG. 6. Abnormal values can be highlighted to the user, for example using different font colors.

Figure 7A:
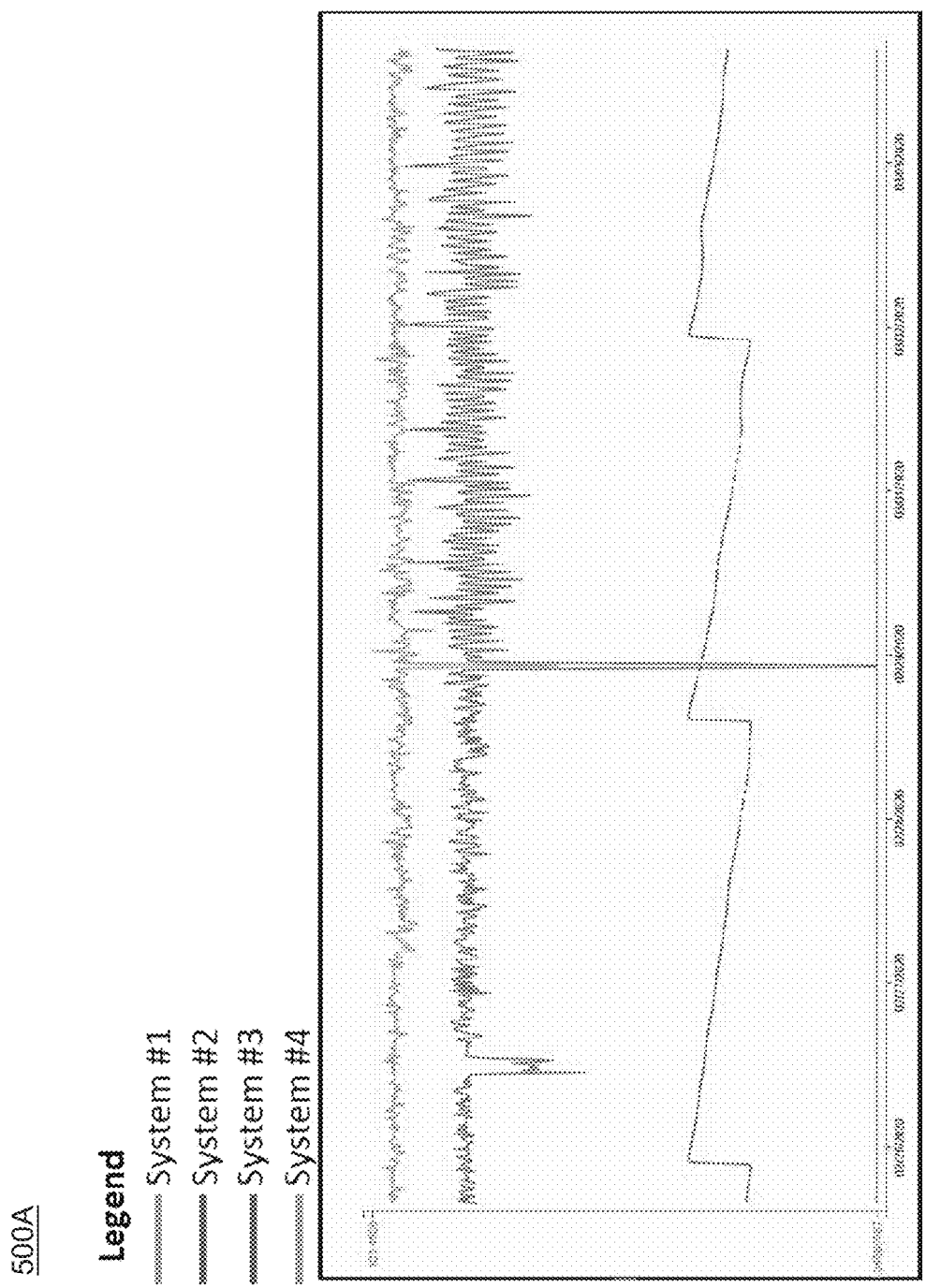
FIGS. 7A-7B show illustrative live user interfaces.
Figure 7B:
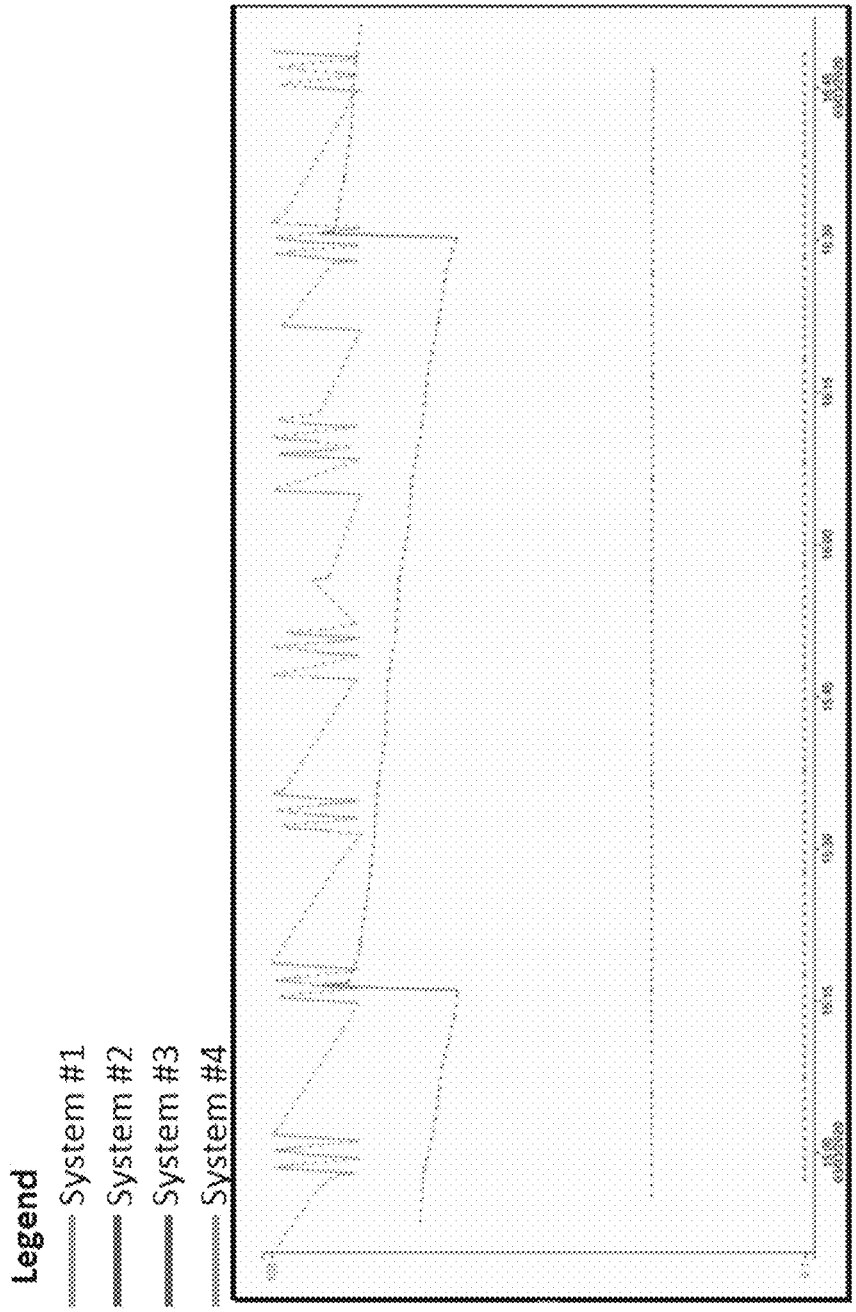

FIGS. 7A-7B show illustrative live user interfaces generated based on pressure data acquired from the pressure sensor, the pressure data being representative of pressure inside the closed system. FIG. 7A shows a user interface 500A including a 7-day plot of pressure monitoring v. time, while FIG. 7B shows a user interface 500B including a 2-hour plot of pressure monitoring v. time. In these examples, multiple fluid pumps are being monitored remotely from different systems (Systems #1, #2, #3 and #4) at the same time. Graph curves can be differently colored to correspond to different systems, in accordance with a legend indicated on the user interface. In illustrative embodiments, an illustrative user interface includes a graphical representation of amperage data over time, the amperage data being acquired from the amperage sensor and being representative of an amperage draw of the motor of the fluid pump.

It will be appreciated by those skilled in the art that the disclosure herein can be embodied in other specific forms without departing from the spirit or essential characteristics thereof. The presently-disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A digital pressure switch configured to be connected to a fluid pump, the digital pressure switch comprising:
    a housing;
    a pressure sensor configured to measure pressure inside a closed system;
    one or more relays configured to be connected to the fluid pump for activation and deactivation of the fluid pump;
    one or more controllers configured to process data from the pressure sensor and to activate or deactivate the motor of the fluid pump based on the data from the pressure sensor, using one or more of the one or more relays;
    a first valve connector configured to connect a plurality of drain valve arrangements disposed outside the housing to a timed drain valve electrical circuit; and
    a second valve connector configured to connect a plurality of unloading valve arrangements disposed inside and outside the housing to an unloading valve electrical circuit.

2. The digital pressure switch of claim 1, wherein the one or more controllers are configured to trigger an alarm based on the data from the pressure sensor.

3. The digital pressure switch of claim 1, further comprising an amperage sensor, wherein the one or more controllers are configured to trigger an alarm based on data from the amperage sensor.

4. The digital pressure switch of claim 1, wherein the one or more relays include two relays.

5. The digital pressure switch of claim 1, in combination with the fluid pump.

6. The digital pressure switch of claim 1, wherein the fluid pump is an air compressor.

7. The digital pressure switch of claim 1, wherein the fluid pump is a water pump.

8. The digital pressure switch of claim 1, wherein the fluid pump is a vacuum pump.

9. The digital pressure switch of claim 1, wherein the closed system includes piping.

10. The digital pressure switch of claim 1, further comprising an on-board battery.

11. The digital pressure switch of claim 1, further comprising a communication module configured to communicate measurement data to an external server.

12. The digital pressure switch of claim 1, further comprising a display and a user input device configured to toggle data displayed on the display.

13. The digital pressure switch of claim 1, further comprising:
    a pressure sensor fitting mounted to the housing and connected to the pressure sensor, wherein
    the pressure sensor is configured to measure the pressure in the closed system through the pressure sensor fitting.

14. The digital pressure switch of claim 1, further comprising:
    a display; and
    a display controller connected to the display and configured to control the display, the display controller being a printed circuit board separate from the one or more controllers, wherein
    the display and the display controller are mounted to the housing in a first orientation relative to the housing and the one or more controllers at a location on the housing, and are configured to be dismounted from the housing and then re-mounted to the housing at the location on the housing in a second orientation opposite the first orientation relative to the housing and the one or more controllers.

15. A method of monitoring a closed system using a digital pressure switch configured to be connected to a fluid pump,
    the digital pressure switch comprising:
    a housing;
    a pressure sensor configured to measure pressure inside the closed system;
    one or more relays configured to be connected to the fluid pump for activation and deactivation of the fluid pump;
    one or more controllers configured to process data from the pressure sensor and to activate or deactivate the motor of the fluid pump based on the data from the pressure sensor, using one or more of the one or more relays;
    a first valve connector configured to connect a plurality of drain valve arrangements disposed outside the housing to a timed drain valve electrical circuit; and
    a second valve connector configured to connect a plurality of unloading valve arrangements disposed inside and outside the housing to an unloading valve electrical circuit,
    the method comprising:
    acquiring first pressure data representative of pressure inside the closed system from the pressure sensor.

16. The method of claim 15, further comprising:
triggering an alarm based on the pressure data using at least one of the one or more relays.

17. The method of claim 15, further comprising:
triggering an alarm based on fluid pump runtime.

18. The method of claim 15, further comprising:
generating a graphical user interface including a graphical representation of the pressure data over time.

19. The method of claim 15, further comprising:
acquiring amperage data acquired from an amperage sensor of the digital pressure switch, the amperage data being representative of an amperage draw of the motor of the fluid pump.

20. The method of claim 19, further comprising:
triggering an alarm based the amperage data.

21. The method of claim 19, further comprising:
generating a graphical user interface including a graphical representation of the amperage data over time.

22. The method of claim 15, wherein the digital pressure switch further comprises:
a pressure sensor fitting mounted to the housing and connected to the pressure sensor, wherein
the pressure sensor is configured to measure the pressure in the closed system through the pressure sensor fitting.

23. The method of claim 15, wherein
the digital pressure switch further comprises:
a display; and
a display controller connected to the display and configured to control the display, the display controller being a printed circuit board separate from the one or more controllers, wherein the display and the display controller are mounted to the housing in a first orientation relative to the housing and the one or more controllers at a location on the housing, and
the method further comprises:
after acquiring the first pressure data, dismounting the display and the display controller from the housing and then re-mounting the display and the display controller to the housing at the location on the housing in a second orientation opposite the first orientation relative to the housing and the one or more controllers, and
after re-mounting the display and the display controller to the housing, acquiring second pressure data representative of pressure inside the closed system from the pressure sensor.

* * * * *